US012708335B2

(12) United States Patent
Fischer et al.

(10) Patent No.: US 12,708,335 B2
(45) Date of Patent: Aug. 18, 2026

(54) POSITRON EMISSION TOMOGRAPHY (PET)-SCANNING DEVICE

(71) Applicant: Positrigo AG, Zürich (CH)

(72) Inventors: Jannis Nikolaus Rudolf Fischer, Zürich (CH); Max Ludwig Ahnen, Zürich (CH)

(73) Assignee: Positrigo AG, Zurich (CH)

( * ) Notice: Subject to any disclaimer, the term of this patent is extended or adjusted under 35 U.S.C. 154(b) by 218 days.

(21) Appl. No.: 18/695,150

(22) PCT Filed: Sep. 22, 2022

(86) PCT No.: PCT/EP2022/076433
§ 371 (c)(1),
(2) Date: Mar. 25, 2024

(87) PCT Pub. No.: WO2023/052247
PCT Pub. Date: Apr. 6, 2023

(65) Prior Publication Data

US 2024/0389959 A1 Nov. 28, 2024

(30) Foreign Application Priority Data

Oct. 1, 2021 (EP) .................................... 21200421

(51) Int. Cl.
*A61B 6/00* (2024.01)
*A61B 6/03* (2006.01)
(Continued)

(52) U.S. Cl.
CPC ............ *A61B 6/4476* (2013.01); *A61B 6/037* (2013.01); *A61B 6/105* (2013.01); *A61B 6/4275* (2013.01); *A61B 6/447* (2013.01)

(58) Field of Classification Search
None
See application file for complete search history.

(56) References Cited

U.S. PATENT DOCUMENTS 5,617,856 A 4/1997 Tamura et al.
7,884,331 B2 2/2011 Majewski et al.
(Continued)

FOREIGN PATENT DOCUMENTS

CN 109864751 A 6/2019
EP 2903524 A1 8/2015
(Continued)

OTHER PUBLICATIONS

"A Look Behind the Machines—How does on make a PET scanner?" Motion Artifacts, Blog by Pearl Technology, Dec. 15, 2023, (9 pages).

(Continued)

*Primary Examiner* — Hoon K Song
(74) *Attorney, Agent, or Firm* — Sughrue Mion, PLLC

(57) ABSTRACT

A positron emission tomography (PET)-scanning device is provided having a detector ring for detecting emitted PET-radiation and a main supporting structure to which is attached a U-shaped portion with two arms for holding the detector ring between the arms (341). The detector ring is held by the two arms in such a way that the detector ring can be rotated about an axis of rotation that extends through the U-shaped portion, in particular through the two arms of the U-shaped portion. The main supporting structure has a guide rail to which the U-shaped portion is attached in such a way, that the U-shaped portion can be displaced along the guide rail, wherein the guide rail extends along an inclined direction relative to the direction of gravity.

20 Claims, 9 Drawing Sheets

(51) Int. Cl.
*A61B 6/10* (2006.01)
*A61B 6/42* (2024.01)

(56) References Cited

U.S. PATENT DOCUMENTS

| | | | | |
|---|---|---|---|---|
| 8,735,834 | B2 | 5/2014 | Millett et al. | |
| 9,226,717 | B2 | 1/2016 | Tashima et al. | |
| 9,414,789 | B2 | 8/2016 | Soluri et al. | |
| 9,833,208 | B2 | 12/2017 | Amano | |
| 10,307,120 | B1 | 6/2019 | Thomas et al. | |
| 10,531,843 | B2 | 1/2020 | Gatayama et al. | |
| 10,653,374 | B1 | 5/2020 | Thomas et al. | |
| 12,171,540 | B2 | 12/2024 | Jang | |
| 2004/0170254 | A1* | 9/2004 | Gregerson | A61B 6/4405 378/197 |
| 2011/0315884 | A1 | 12/2011 | Worstell et al. | |
| 2013/0218010 | A1 | 8/2013 | Weinberg et al. | |
| 2015/0115162 | A1 | 4/2015 | Tashima et al. | |
| 2016/0166219 | A1 | 6/2016 | Majewski et al. | |
| 2018/0011153 | A1 | 1/2018 | Pourrahimi | |
| 2018/0177473 | A1* | 6/2018 | Gregerson | A61B 6/0407 |
| 2018/0199853 | A1 | 7/2018 | Abkai et al. | |
| 2023/0355194 | A1* | 11/2023 | Gregerson | A61B 6/035 |
| 2024/0324976 | A1 | 10/2024 | Fischer et al. | |
| 2025/0009315 | A1 | 1/2025 | Ahnen et al. | |

FOREIGN PATENT DOCUMENTS

| | | | |
|---|---|---|---|
| JP | 2000-214263 | A | 8/2000 |
| JP | 3244776 | B2 | 1/2002 |
| JP | 3793320 | B2 | 7/2006 |
| JP | 2010-223956 | A | 10/2010 |
| JP | 4642143 | B2 | 3/2011 |
| WO | 2014/058772 | A1 | 4/2014 |
| WO | 2018/098147 | A1 | 5/2018 |
| WO | 2020/015384 | A1 | 1/2020 |

OTHER PUBLICATIONS

FDA, FDA 501K Response from the US Food and Drug Administration dated Jul. 15, 2024, Retrieved from Internet: https://www.accessdata.fda.gov/cdrh_docs/pdf24/K241751.pdf, (13 pages).

Seiichi Yamamoto et al, "Development of a Brain PET System, PET-Hat: A Wearable PET System for Brain Research", IEEE Transactions on Nuclear Science, Jun. 2011, p. 668-673, vol. 58, No. 3.

International Search Report for PCT/EP2022/076433 dated Nov. 8, 2022.

Written Opinion for PCT/EP2022/076433 dated Nov. 8, 2022.

* cited by examiner

POSITRON EMISSION TOMOGRAPHY (PET)-SCANNING DEVICE

CROSS REFERENCE TO RELATED APPLICATIONS

This application is a National Stage of International Application No. PCT/EP2022/076433 filed Sep. 22, 2022, claiming priority based on European Patent Application No. 21200421.2 filed Oct. 1, 2021.

TECHNICAL FIELD

The present invention concerns a positron emission tomography (PET)-scanning device, which is particularly well adaptable to the needs of the subject to be scanned.

PRIOR ART

Positron emission tomography (PET)-scanning devices are usually big and bulky and only available at hospitals or at dedicated radiology facilities. As a consequence, patients have to travel to the place of the PET-scanning device, in order to be scanned, if required. The patients, however, are often elderly or sick people who live in a nursing home, cannot move well or are confined to bed. As a result, the travel to the PET-scanning location is cumbersome for the patients and often involves a not inconsiderable risk that the patient may have a complication while traveling or becomes infected, for example. Thus, most state of the art PET-scanning machines have the drawback that they cannot be brought to subjects.

The PET-scanning device also requires the patient to assume a certain position, usually a position lying on the back, on a bed during the scanning procedure. Depending on his state of health, this position can be quite a burden for the patient, which can even impair the scanning result, if the patient e.g. moves during the scanning.

Furthermore, hospitals, researchers, material scientists and veterinarians have no good access to PET-machines, not only because they are too big, but also because they often do not fit their needs in particular with regard to applications outside of the standard oncology applications in the hospital clinic.

A large portion of PET-scanning is related to the imaging of the human brain. For this purpose, however, a whole body PET-scanner with a large bore to fit the entire human body is often used. As a consequence, the detector elements are arranged further away from the area to be imaged, which results is less sensitivity and specificity.

US 2013/0218010 A1 discloses a compact and light-weight PET-scanner which is portable and can be affixed to a patient bed.

In WO 2020/015384 A1, U.S. Pat. No. 9,226,717 B2, U.S. Pat. No. 7,884,331 B2 and CN 109864751 A, a PET-detector is disclosed that is integrated in a helmet-like brain imager. The PET brain imager is suspended from a mobile gantry.

U.S. Pat. No. 9,833,208 B2 discloses a PET-imaging device with an adjustable support table, which allows the patient to either sit, lie or stand during the imaging procedure.

The PET-scanning device as disclosed in U.S. Pat. No. 10,307,120 B1 comprises a horizontally positioned and vertically movable detector ring which enables the patient to sit upright in a wheel chair during the scanning process.

JP 3244776 B2 shows a computer tomography (CT)-machine with a gantry body that can be inclined by rotating it about an upper, horizontally extending axis, in order to enable a scanning of patients in both sitting and lying positions.

U.S. Pat. No. 10,531,843 B2 proposes to combine a CT apparatus having a horizontally rotatable gantry device with an adjustable scanning support that allows the patient to adopt any of a variety of different positions during the imaging process.

U.S. Pat. No. 9,414,789 B2 shows a PET-imaging device with reduced dimensions. The device comprises a plurality of measuring rings with different diameters, which are slidably mounted on a support structure.

US 2011/0315884 A1 discloses a mobile PET-scanner on wheels for imaging the human head. Another mobile PET-scanner on wheels is disclosed by U.S. Pat. No. 8,735,834 B2.

JP 4642143 B2 discloses a PET-scanning device with a detector ring that is held between two arms which are suspended via a pulley on a ceiling or via linked rods on a wall or on a wheel chair.

US 2016/0166219 A1 is directed to a device that combines a virtual reality system with PET-brain imaging. A mobile brain imager is suspended on a mobile support which can be carried in the form of a backpack or which can be arranged on a carriage having wheels.

JP 3793320 B2 shows a CT-machine having a U-shaped support structure to which two vertically movable holding arms are attached. A rotatable imaging unit is held between the two arms.

WO 2014/058772 A1 discloses an apparatus for cone beam computed tomography having a gimballed scanner device that houses source and detector. The scanner device is movable along a vertical support column.

SUMMARY OF THE INVENTION

It is an object of the present invention to provide a versatile positron emission tomography (PET)-scanning device which can be easily adapted to the needs of the subject to be scanned.

For the purposes of this document, height and directional information, such as “top”, “bottom”, “up”, “down”, “upwards”, “downwards”, etc., shall be understood to refer to a PET-scanning device which, in its normal and intended use, stands upright in relation to the direction of gravity, ready to scan a human or animal subject or a plant.

In order to achieve this objet, the present invention provides a positron emission tomography (PET)-scanning device comprising

- a detector ring for detecting emitted PET-radiation; and
- a main supporting structure to which is attached a U-shaped portion with two arms for holding the detector ring between the arms;
- wherein the detector ring is held by the two arms in such a way that the detector ring can be rotated about an axis of rotation that extends through the U-shaped portion, in particular through the two arms of the U-shaped portion.

The main supporting structure comprises a guide rail which extends along an inclined direction relative to the direction of gravity and to which the U-shaped portion is attached in such a way, that the U-shaped portion can be displaced along the guide rail.

By extending along an inclined direction relative to the direction of gravity it is meant that the guide rail extends neither in parallel, i.e. at an angle of 0°, nor perpendicularly, i.e. at an angle of 90°, with respect to the direction of gravity.

Instead, the guide rail extends at an angle of preferably between 0° and 60°, more preferably between 10° and 50°, most preferably between 20° and 40°, with respect to the direction of gravity. The inclined extension of the guide rail has the consequence that the U-shaped portion, together with the detector ring, are displaceable, with respect to the main supporting structure, along an inclined direction relative to the direction of gravity.

The possibility of displacing the detector ring along an inclined or oblique direction with respect to the direction of gravity allows to optimally position the detector ring with respect to a patient to be scanned, while the patient is in a comfortable lying or leaning sitting position. Thus, with the PET-scanning device as indicated it is not the patient who needs to be positioned with respect to the detector ring, but the detector ring can be positioned such, that the region-of-interest can be optimally imaged without having to move the patient. For the patients, especially for elder patients, it has turned out that particularly a leaning sitting position is comfortable during the imaging procedure. It is a natural position, which leads to less movements of the patient especially during longer imaging sessions. The displaceability of the detector ring along an inclined direction allows positioning the detector ring along the longitudinal main axis of the upper part of the body of the such positioned patient and the rotatability enables an optimal orientation of the detector ring with respect to the desired imagining plane.

Furthermore, the ability to rotate the detector ring relative to the U-shaped portion in combination with the ability to displace the U-shaped portion along an inclined direction, leads to a high versatility of the PET-scanning device. With these abilities, the PET-scanning device is not only adapted to scan human patients, in particular human brains, but it is also suited to scan extremities, such as arms and legs, and/or to scan animals or plants. The possibility to rotate and displace the detector ring relative to the main supporting structure makes the PET-scanning device particularly versatile and adaptable to different purposes, such as to e.g. the scanning of rodents or of plants. It is therefore preferred that the detector ring can be rotated such that it can be oriented, with its opening, in both a horizontal and a vertical position.

By providing a U-shaped portion for holding the detector ring, a relatively simple construction of the PET-scanning device becomes possible, which allows to both displace and rotate the detector ring. The U-shaped portion preferably represents the only element, which mechanically connects the detector ring to the main supporting structure.

The extension of the axis of rotation of the detector ring through the two arms brings about the advantage that the detector ring can be adjusted easily to the patient's needs by means of rotation, while at the same time be held in a particularly stable way on the main supporting structure. No unnecessary elements need to be rotated with the detector ring, which allows to reduce the total weight of the rotatable parts and to make the rotation of the detector ring easier for the user.

It is conceivable that in certain embodiments, the detector ring is not only displaceable with the U-shaped portion, but also relative to the U-shaped portion, in particular relative to the two arms. The additional displaceability of the detector ring relative to the U-shaped portion can for example be provided in order to enable fine adjustments.

The detector ring usually comprises a plurality of sensors, in particular a plurality of sensor modules, which are arranged in a circumferential ring, in order to be positioned around e.g. a patient's head for detecting PET-radiation emitted from the patient's brain. The detector ring preferably forms a closed ring, i.e. it is closed in the circumferential direction. By forming a closed ring, the sensors can be optimally arranged along the entire inner surface of the detector ring.

The detector ring usually has a round, for example oval or circular, shape at least at its inner surface. Thus, the detector ring usually and preferably has a round, in particular circular, opening, into which the part to be scanned of the subject is inserted for the PET-scanning. The outer surface of the detector ring preferably also forms a round, in particular circular, shape. A detector ring having such a form has a more lightweight look in the eyes of the user. The detector ring can, however, also have an angular, in particular rectangular or squared, inner and/or outer shape.

The detector ring advantageously has at least one handle for facilitating rotation and displacement of the detector ring for the user. The PET-scanning device can, however, also have one or several motor units, which serve for displacing and/or rotating the detector ring. In this case, it would also be conceivable that the handle for rotation and displacement would be omitted.

In normal use of the PET-scanning device, the main supporting structure usually carries the main weight, if not the entire weight, of the detector ring. Thus, the main supporting structure usually serves to support and to hold the detector ring in a stable position during the scanning procedure. After having positioned the main supporting structure close to the subject to be scanned or vice versa, the detector ring can be rotated and displaced accordingly, in order to adjust the PET-scanning device to the subject.

The U-shaped portion is defined by the two arms in particular. The two arms are usually connected to each other at one end by means of a perpendicularly extending connection portion, which also forms a part of the U-shaped portion. The other end of each arm usually forms a free end. The axis of rotation extends through the U-shaped portion, if it extends through at least one out of the connection portion and the two arms. Preferably, the axis of rotation extends through each of the two arms. Particularly preferred are embodiments in which the axis of rotation extends in a perpendicular direction with respect to the direction of extension of the two arms and advantageously in parallel to the connection portion. Swivel joints are preferably arranged on each of the two arms, in order to enable the rotation of the detector ring.

The two arms and the connection portion preferably define a plane within which the U-shaped portion is arranged. The plane can have a certain thickness. Elements that are not arranged within this plane and that particularly extend in a perpendicular direction relative to this plane are normally not considered to be part of the U-shaped portion, in particular, if these elements are displaceably attached. The U-shaped portion preferably forms a mechanically fixed structural unit of the PET-scanning device, i.e. it does not comprise any parts that are movable relative to each other.

The direction of displacement preferably extends perpendicularly to the direction along which two arms extend, in particular perpendicularly to the direction along which the two arms extend from the connection portion to their free ends. For this purpose, the two arms of the U-shaped portion preferably extend obliquely upwards in relation to the direction of gravity. In order to be optimally adjustable to the desired imaging plane, the detector ring is advantageously, in at least one rotation position, displaceable in a direction that stands approximately perpendicular to the plane defined by opening of the detector ring.

In a particularly preferred embodiment, the main supporting structure and the U-shaped portion together form a Z-shaped structure. A Z-shaped structure allows a particularly stable design of the PET-scanning device.

Preferably, the PET-scanning device additionally comprises a weight-compensation device for compensating the weight of the U-shaped portion and the detector ring, in order to facilitate the displacement of the U-shaped portion along the guide rail for the user. For this purpose, the weight-compensation-device preferably comprises a counterweight, which is connected to the U-shaped portion via a pulley. The pulley can particularly be arranged on top of the main supporting structure. The counterweight is preferably arranged on the opposite side of the main supporting structure with respect to the U-shaped portion. The main supporting structure can comprise a further guide rail to which the counterweight is attached in such a way, that the counterweight can be displaced along the further guide rail. The further guide rail preferably extends along an inclined direction relative to the direction of gravity and in particular in parallel to the guide rail to which the U-shaped portion is attached.

The guide rail to which the U-shaped portion is attached and/or the further guide rail to which the counterweight is attached can each comprise two or more rail elements which extend in parallel to each other, in order to distribute the weight of the U-shaped portion and the detector ring or of the counterweight, respectively.

A first motor unit can be provided, in order to displace the U-shaped portion along the guide rail. Alternatively or additionally, a second motor unit can be provided for rotating the detector ring about the axis of rotation. The provision of the first and/or the second motor unit advantageously not only facilitates the handling of the PET-scanning device for the operating personnel, but preferably also allows the detector ring to be displaced and rotated remotely relative to the subject to be imaged.

The PET-scanning device preferably comprises a first brake device for preventing an undesired displacement of the U-shaped portion along the guide rail. Thus, by means of the first brake device, the displacement position of the detector ring relative to the main supporting structure can be fixed. In a preferred embodiment, the first brake device comprises one or more brake pads that are attached to the U-shaped portion and are adapted to act directly on the guide rail, in order to achieve a braking effect. The first brake device can particularly be an electromagnetically actuated brake device, which generates a braking effect when not activated and releases the braking effect upon activation. Thus, for safety reasons, only with an electrical current being provided to the first brake device, it is preferably possible to displace the detector ring together with the U-shaped portion.

Alternatively or additionally, the PET-scanning device can comprise a second brake device for preventing an undesired rotation of the detector ring about the axis of rotation. Thus, by means of the second brake device, the rotational position of the detector ring relative to the U-shaped portion can be fixed. For this purpose, the second brake device can for example act on one or both of the swivel joints, in which the detector ring is attached to the U-shaped portion, in order to generate the braking effect. The second brake device can particularly be an electromagnetically actuated brake device, which generates a braking effect when not activated and releases the braking effect upon activation. Thus, for safety reasons, only with an electrical current being provided to the second brake device, it is preferably possible to rotate the detector ring.

In certain preferred embodiments, the PET-scanning device can comprise wheels that are attached to the main supporting structure, in order to make it easier to move the PET-scanning device. The wheels make it possible to move the PET-scanning device and to bring it to the subject to be scanned, instead of bringing the subject to the PET-scanning device. If wheels for moving the PET-scanning device are provided, the device preferably also comprises a wheel locking mechanism, in order to avoid undesired movements of the PET-scanning device particularly during the scanning of a subject.

Due to its movability, the PET-scanning device also enables in-room monitoring during a hadron therapy. For this purpose, the patient can be moved on the treatment support directly into the detector ring, which has preferably been positioned at the correct height and has been co-registered with the hadron therapy device beforehand, in order to not lose valuable time and signal from isotopic tracer decay.

The axis of rotation, about which the detector ring can be rotated, preferably extends through the centre of mass of the detector ring. The detector ring can then be rotated particularly easily by the user and/or by the second motor unit and the load acting on the constructional components is minimized. Particularly preferred is an embodiment, in which the axis of rotation extends diametrically through the detector ring. Thus, the detector ring is preferably attached at two diametrically arranged positions of its outer surface to the two arms of the U-shaped portion.

In order to balance the centre of mass of the detector ring with respect to the axis of rotation, the PET-scanning device preferably comprises one or more weights, which are movably attached to the detector ring and/or which are detachably attachable to the detector ring.

In order to be able to position and orient the detector ring with respect to the imaged subject in an exact and reproducible way, the PET-scanning device preferably comprises one or more detector encoders, in particular one or more electronic detector encoders, for detecting the displacement position of the U-shaped portion along the guide rail and/or the rotation angle of the detector ring about the axis of rotation. The electronic detector encoders are preferably connected to a computing device which is used to carry out an acquisition of PET-related data by means of the detector ring.

In other also preferred embodiments, the PET-scanning device can comprise a scanning support in the form of for example a seating unit, i.e. a chair, or a bed, in order to accommodate the subject to be scanned. The main supporting structure can be, but does not need to be formed in one piece with the scanning support. If it is not formed in one piece with the main supporting structure, the scanning support preferably comprises positioning means, that allow the scanning support to be positioned in a well-defined, exact and reproducible way with respect to the main supporting structure. The scanning support is preferably adjustable to the needs of the subject to be scanned. If the scanning support is in the form of a seating unit, then it preferably comprises a backrest that extends in parallel to the guide rail along which the U-shaped portion is displaceable.

The preferably adjustable scanning support, in particular the adjustable seating unit, preferably comprises one or more support encoders, in particular one or more electronic support encoders, for detecting the position of the patient. The electronic support encoders are preferably connected to a computing device which is used to carry out an acquisition of PET-related data by means of the detector ring. If the scanning support is not formed in one piece with the main supporting structure and if the computing device is arranged at the side of the main supporting structure, coupling elements are preferably provided, in order to connect the support encoders to the computing device. The support encoders can for example be adapted to detect the height of a seating surface, the height of a headrest, the height of a backrest of the seating unit and/or the angle of inclination of one or more of these parts.

In certain embodiments, the scanning support can be adapted to position a patient's breast within the detector ring. Thus, the scanning support is in this case particularly adapted for scanning the patient's breast by means of the sensors of the detector ring. This application is particularly suited in the field of oncology. The scanning support preferably comprises an opening or an indentation which, during the PET-imaging procedure, allows the breast to hang into the opening or to rest on the support, respectively. Thus, the opening or indentation, whichever applies, is preferably oriented or orientable horizontally with respect to gravitation.

The PET-scanning device can additionally comprise an adjustable headrest, which allows a human patient to be placed in a lying and/or sitting position for the PET-scanning procedure. The headrest serves to position and hold the patient's head during the scanning procedure. For this purpose, the headrest, which is preferably adapted to be arranged inside of the detector ring, can be attached to the detector ring or to the scanning support.

The headrest can comprise one or more fixation elements for fixating the head, in particular fixation elements that can be used in combination with means for fixation used in stereotactic radiosurgery and hadron beam therapy which means comprise e.g. stereotactic head frames and/or thermoplastic face masks that are attachable to patient frames.

The PET-scanning device can have an overall outer shape which narrows from the U-shaped portion downwards along the direction of gravity, in particular when viewed from a frontal direction perpendicular to the axis of rotation. With such a design, the PET-scanning device can be particularly space-saving, because the width of the device is mainly defined, at least in the upper region, by the width of the U-shaped portion needed for holding the detector ring. At the bottom, the outer shape of the PET-scanning device can broaden again along the direction of gravity, in order to improve the stability.

The PET-scanning device preferably has overall dimensions that allow the device, at least in one position of the detector ring, to be moved in its normal upright position through a standard door opening having a width of not more than 98.5 cm, in particular of not more than 86.0 cm. More preferably, if the PET-scanning device has wheels, the device has an overall width that allows the PET-scanning device to be rolled through a door opening having a width of not more than 98.5 cm, in particular of not more than 86.0 cm The PET-scanning device preferably additionally comprises a computing device for carrying out an acquisition of PET-related data by means of the detector ring. The computing device usually comprises at least a processor, in particular a central processing unit, and a storage element. Pre-defined instructions are usually pre-stored in the storage element for instructing the PET-scanning device to detect emitted PET-radiation by means of the detector ring and to safe or at least cache the acquired PET-information and/or to further transmit the information to another device, e.g. by means of a wired or wireless transmission unit. The computing device is preferably integrated in the main supporting structure.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Figure 1:
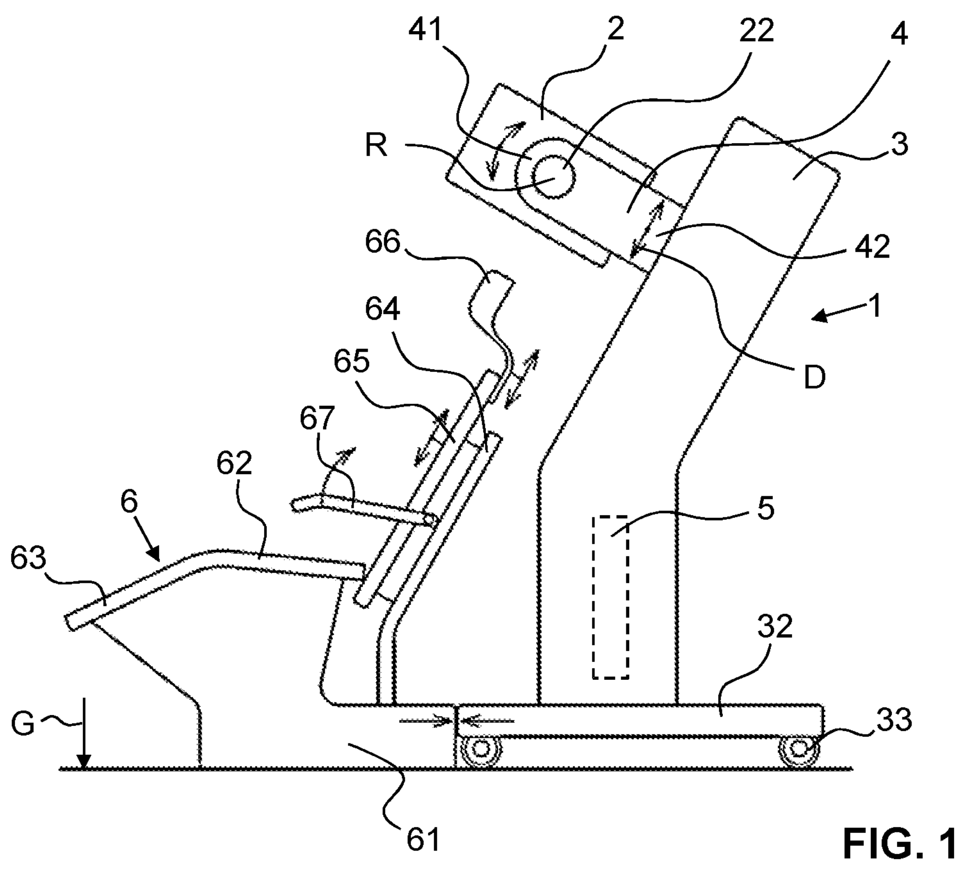
FIG. 1 shows a schematic side view of an inventive PET-scanning device according to a first embodiment with a support device in the form of a seating unit.

In FIGS. 1 to 14, several different embodiments of an inventive PET-scanning device 1 are shown. Elements that have the same or a similar function, but belong to different embodiments, are annotated with the same reference numerals in each case.

In all embodiments as shown in FIGS. 1 to 14, the PET-scanning device 1 comprises a detector ring 2, which has a plurality of sensors arranged along of its circular inner surface. The sensors, which are not visible in the figures, serve to detect and measure the PET-radiation emitted in the region of the opening of the detector ring 2. The detector ring 2 has the basic shape of a ring in each case, with a circular inner and outer surface.

In all of the embodiments, the detector ring 2 is arranged between two holding arms 41 that hold the detector ring 2 between them. The two holding arms 41 form a part of a U-shaped portion 4, which is attached to a main supporting structure 3. The detector ring 2 is rotatable about an axis of rotation R that extends through the two holding arms 41 of the U-shaped portion 4. Furthermore, the detector ring 2 is displaceable together with the U-shaped portion 4 along an inclined direction D relative to the main supporting structure 3 in all embodiments. In order to facilitate rotation and displacement of the detector ring 2, one or several handles can be attached to the outer surface of the detector ring 2.

The direction along which the U-shaped portion 4 is displaceable is inclined with respect to the direction of gravity G, meaning that it is neither parallel nor perpendicular to the direction of gravity G. In all embodiments, the U-shaped portion 4 is attached to a guide rail that is provided on the main supporting structure 3 and allows the U-shaped portion 4 to be displaced along the inclined direction D as mentioned. Thus, the guide rail also extends along the inclined direction.

The axis of rotation R extends along a horizontal direction, i.e. perpendicularly to the direction of gravity G. Furthermore, the axis of rotation R extends perpendicularly to the direction along which the U-shaped portion 4 can be displaced. The displacement direction D is approximately perpendicular to the longitudinal extension of the holding arms 41.

In the first embodiment shown in FIG. 1, the main supporting structure 3 comprises a lower vertical portion and an upper inclined portion. The U-shaped portion 4 is attached to the upper side of the upper inclined portion of the main supporting structure 3 in such a way, that the U-shaped portion 4 is displaceable along the entire length of the upper inclined portion. The two holding arms 41 of the U-shaped portion 4 serve to hold the detector ring 4 between them. For this purpose, two fixation lugs 22 are attached to the outer surface of the detector ring 2. The fixation lugs 22 are provided on diametrically opposite sides of the detector ring 2. The fixation lugs 22 engage with a through-hole in each of the holding arms 41.

The engagement of each fixation lug 22 and the respective through-hole is such, that a rotation of the detector ring 2 about the axis of rotation R is enabled. The axis of rotation R is defined by the position of the fixation lugs 22. Thus, the axis of rotation R extends centrally through each of the two fixation lugs 22 and through each of the holding arms 41. With regard to the detector ring 2, the axis of rotation R extends diametrically through the ring and preferably through the centre of mass of the detector ring 2.

For carrying out the PET-image acquisition, a computing device 5 is accommodated within the main supporting structure 3. Data and/or energy transmission to or from the computing device 5 can be done via one or several cables and/or wirelessly. In other embodiments, the computing device 5 could also be arranged externally. The computing device 5 is preferably connected, by cable or wirelessly, to a user input and output device. The user input and output device can for example be in the form of an external personal computer or it can be a display, in particular a display with a touch screen, which is attached to the PET-scanning device.

A scanning support 6 is provided for accommodating a human patient in an inclined sitting position during the scanning procedure. The scanning support 6 can be, but does not need to be, part of the PET-scanning device 1. Prior to the image acquisition, the patient is accommodated on the scanning support 6 with the detector ring 2 being in the uppermost position of the main supporting structure 3. The detector ring 2 is then rotated and displaced by the medical personnel into an optimal position for the image acquisition using the handle(s) (not shown in FIG. 1).

The scanning support 6 in the form of a chair-like seating unit comprises a base structure 61 that supports a seat base 62 and a leg support 63 for supporting the legs of the patient during the scanning procedure. Also attached to the base structure 61 is an inclined back support 64. Attached to the upper side of the back support 64 are a backrest 65 and pivotable (see arrow in FIG. 1) armrests 67. The backrest 65 can be displaced along the back support 64 (double arrow in FIG. 1), in order to optimally accommodating the patient during the PET-scanning procedure. At the upper end, a headrest 66 is attached to the backrest 65 in such a way, that a displacement of the headrest 66 along the longitudinal direction of the backrest 65 is possible (double arrow in FIG. 1), in order to further adjust the scanning support 6 to the patient. For the image acquisition, the head of the patient rests on the headrest 66 and the detector ring 2 is displaced and rotated such that the patient's head is arranged inside of the detector ring 2. Thus, the headrest 66 is likewise arranged inside of the detector ring 2 during the imaging process.

The displacement direction D of the detector ring 2, which is defined by the longitudinal extension of the guide rails (not shown in FIG. 1) that are attached to the main supporting structure 3, approximately corresponds to the longitudinal extensions of the back support 64 and of the backrest 65 as well as to the directions along which the back support 64 and the backrest 65 are displaceable. Thus, the displacement direction D of the detector ring 2 corresponds to the longitudinal main axis of the upper part of the body of the patient, if the patient sits in the scanning support 6 as intended and is ready for the scanning procedure. In order to prevent the patient from moving his head during the image acquisition, a head strap can be used.

In the embodiment of FIG. 1, the scanning support 6 is separate from the rest of the PET-scanning device 1 and in particular from the main supporting structure 3. The main supporting structure 3 of the PET-scanning device 1 comprises a base structure 32, to which wheels 33 are attached. By means of the wheels 33, the PET-scanning device 1 can be moved, in order to bring it to the patient. The scanning support 6 does not have any wheels here. Thus, the location of the scanning support 6 is fixed, which has the advantage that the external parameters and conditions are well-defined and known with regard to the scanning procedure. In such a setting, the PET-scanning device 1 can e.g. be used in combination with one or more such scanning supports 6, in order to use the same PET-scanning device 1 for carrying out PET-scans at several designated locations of e.g. a hospital or a nursing home. Positioning means are preferably provided, that allow the main supporting structure 3 to be positioned in a well-defined, exact and reproducible way with respect to the scanning support 6.

As can be seen from the lateral view of FIG. 1, the U-shaped portion 4 and the main supporting structure 3 including the base structure 32 together form a Z-shaped structure. The stability of the PET-scanning device 1 is optimized by this shape.

The two holding arms 41 of the U-shaped portion 4 are connected on one end by a connection portion that is here referred to as the holding base 42. From the holding base 42, the two holding arms 41 extend in parallel in an obliquely upward direction with respect to the direction of gravity G. The holding base 42 extends in a perpendicular direction with respect to the two holding arms 41. During the acquisition of PET-scanning images, the head of the patient is located in the area between the two holding arms 41.

Figure 2:
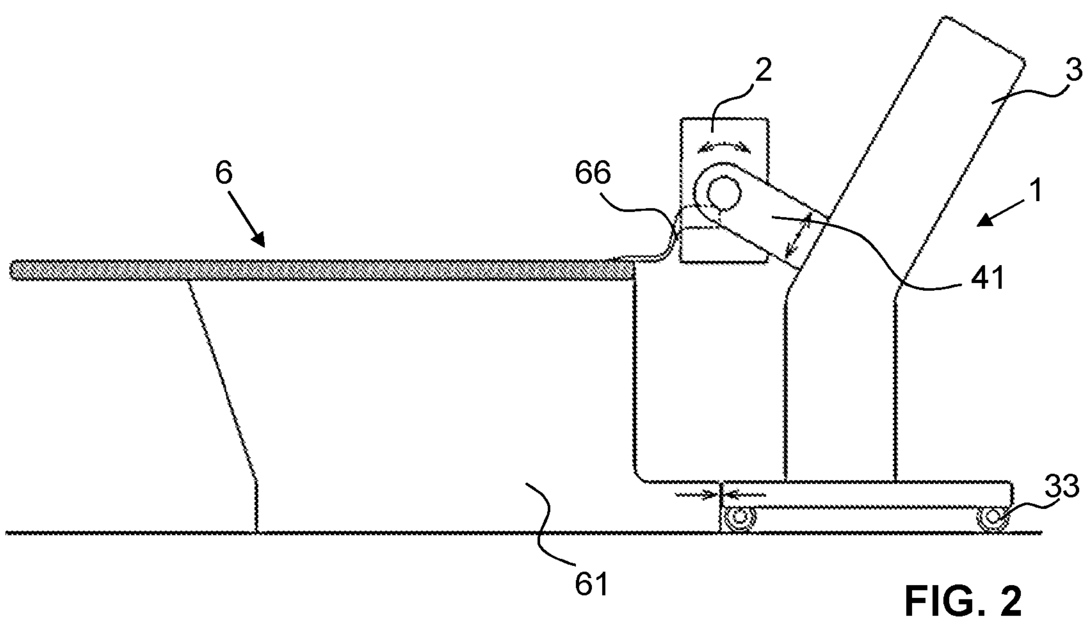
FIG. 2 shows a schematic side view of the same PET-scanning device as in FIG. 1, with a support device on that allows imaging of a patient in a lying position.

FIG. 2 shows the use of the same PET-scanning device 1 as in FIG. 1 in combination with a scanning support 6 which is here in the form of a bed. Thus, the PET-scanning device 1 can not only be used to scan patients in the sitting position as shown in FIG. 1, but also to scan patients in the lying position as shown in FIG. 2. Due to its displaceability and rotatability with respect to the main supporting structure 3, the detector ring 2 can be optimally positioned in both cases.

Figure 3:
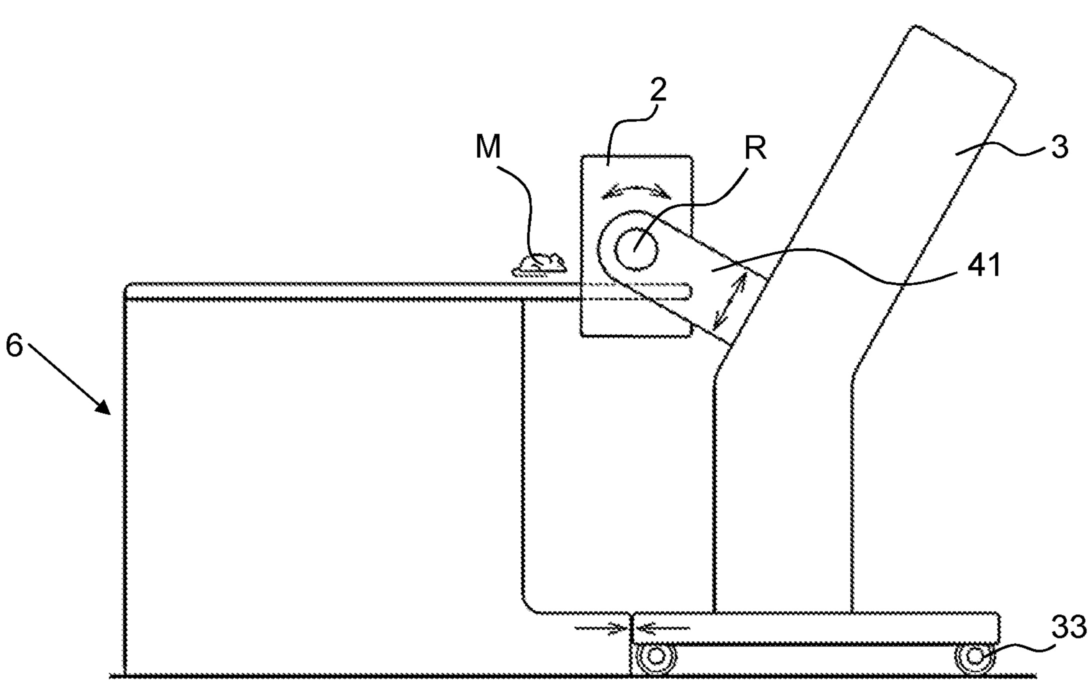
FIG. 3 shows a schematic side view of the same PET-scanning device as in FIG. 1, with a support device for the imaging of rodents.
Figure 4:
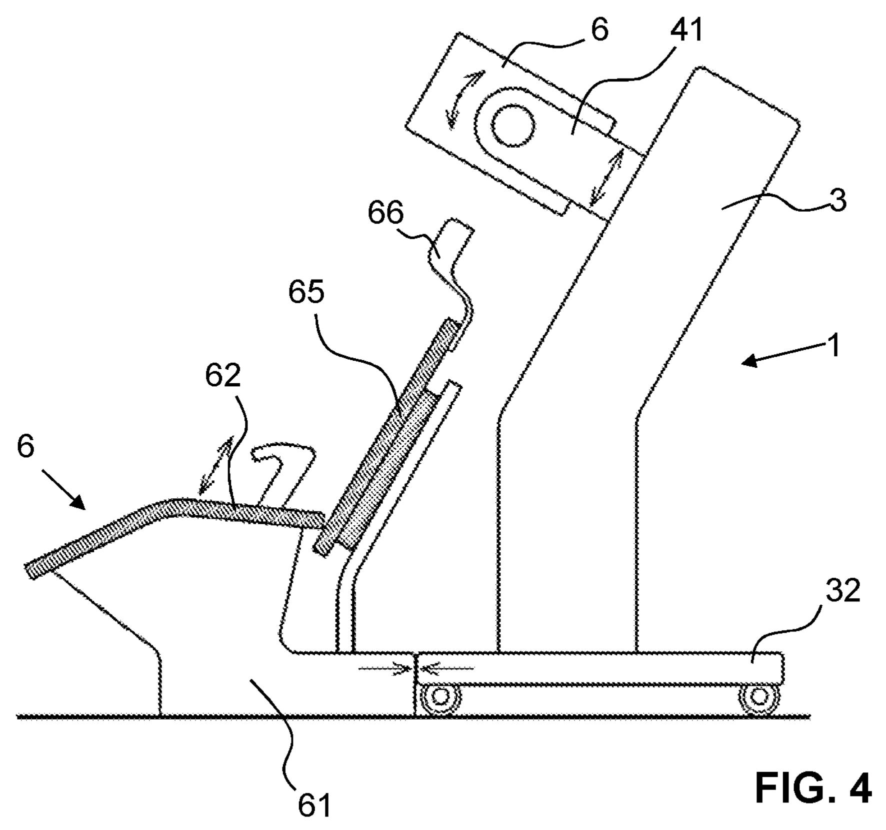
FIG. 4 shows a schematic side view of the same PET-scanning device as in FIG. 1, with another variant of a seating unit.

In FIG. 3, the same PET-scanning device 1 as in FIG. 1 is used for scanning rodents, i.e. a mouse M in the present case. As in the case of FIG. 2, for this purpose, the detector ring 2 is displaced to a lower position with respect to the main supporting structure 3 and rotated about the axis or rotation R in a vertical position. With this position and orientation of the detector ring 2, it is possible to move the rodents to be scanned completely from one side to the other through the opening of the detector ring 2. The height-adjustment and the rotatability of the detector ring 2 not only allows the PET-scanning device 1 to be optimally adjusted to the scanning situation, but also to store it in a particularly space-saving way.

FIG. 4 shows once again the same PET-scanning device as in FIG. 1, but with another variant of a scanning support 6. In the present case, the seat base 62 and leg support 63 are height-adjustable, instead of the backrest 65 and the headrest 66.

Figure 5:
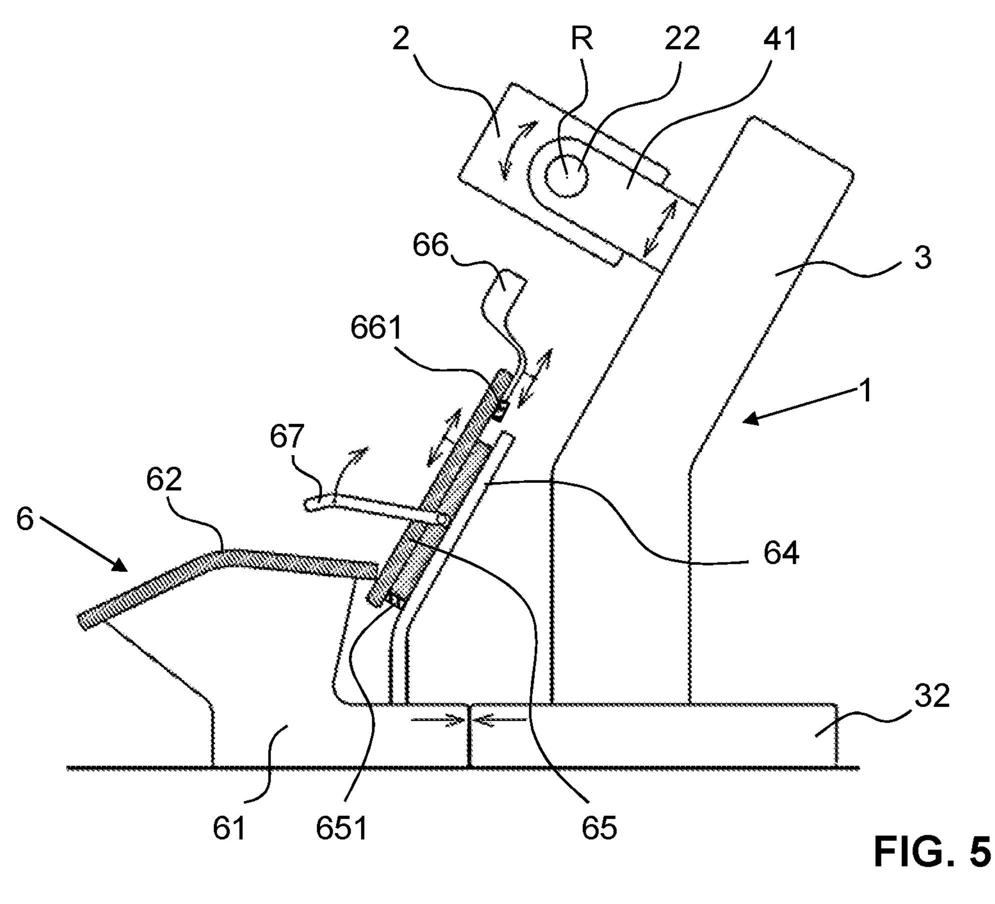
FIG. 5 shows a schematic side view of an inventive PET-scanning device according to a second embodiment, with the seating unit of FIG. 4.

FIG. 5 shows a PET-scanning device 1 according to a further embodiment, which differs from the one of FIG. 1 by not having any wheels. Thus, the PET-scanning device 1 is here designed to be stationary. Instead of the PET-scanning device 1, the scanning support 6 can have wheels, in order to be mobile, or it can be stationary as well, as in the case of FIG. 5.

The scanning support 6 shown in FIG. 5 comprises encoders in the form of a backrest position encoder 651 and of a headrest position encoder 661, in order to detect and measure the position of the patient with respect to the PET-scanning device 1 and in particular with respect to the main supporting structure 3. The backrest position encoder 651 is adapted to detect the position of the backrest 65 with respect to the back support 64 and the headrest position encoder 661 is adapted to detect the position of the headrest 66 with respect to the backrest 65. The two encoders 651 and 661 are preferably connected by cable or wirelessly with the computing device 5. Couplings can be provided in the area where the base structure 61 of the scanning support 6 contacts the base structure 32 of the main supporting structure 3, in order to enable the data transfer between the encoders 651, 661 and the computing device 5, if the latter is arranged within the main supporting structure 3. Encoders for detecting the position of the subject to be scanned on the scanning support can of course also be provided in all other embodiments.

Figure 6:
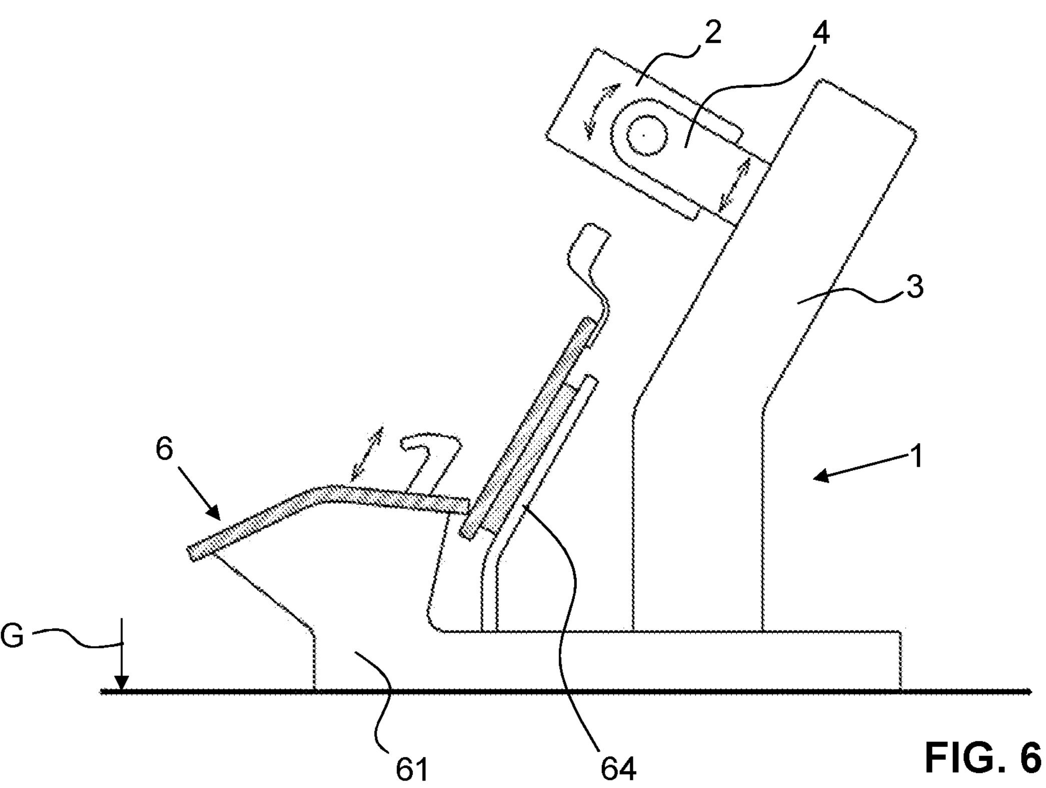
FIG. 6 shows a schematic side view of an inventive PET-scanning device according to a third embodiment, with a seating unit that is fixedly attached to the main supporting structure.

FIG. 6 shows another embodiment of a PET-scanning device 1, in which the main supporting structure 3 is made in one piece with the scanning support 6. This embodiment has the advantage that the relative positions of the main supporting structure 3 and the scanning support 6 are well defined and cannot be changed.

Figure 7:
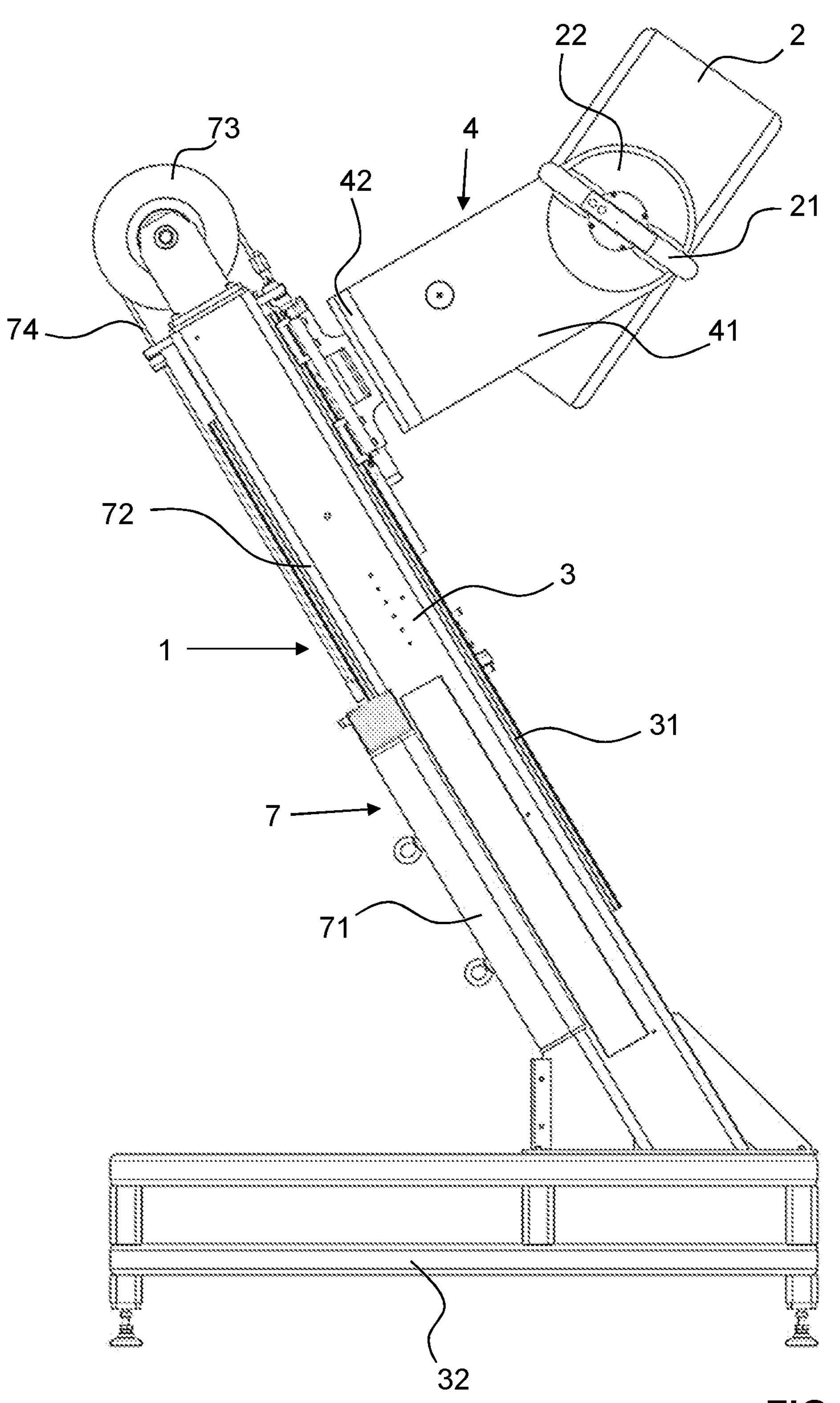
FIG. 7 shows a side view of an inventive PET-scanning device according to a fourth embodiment.
Figure 8:
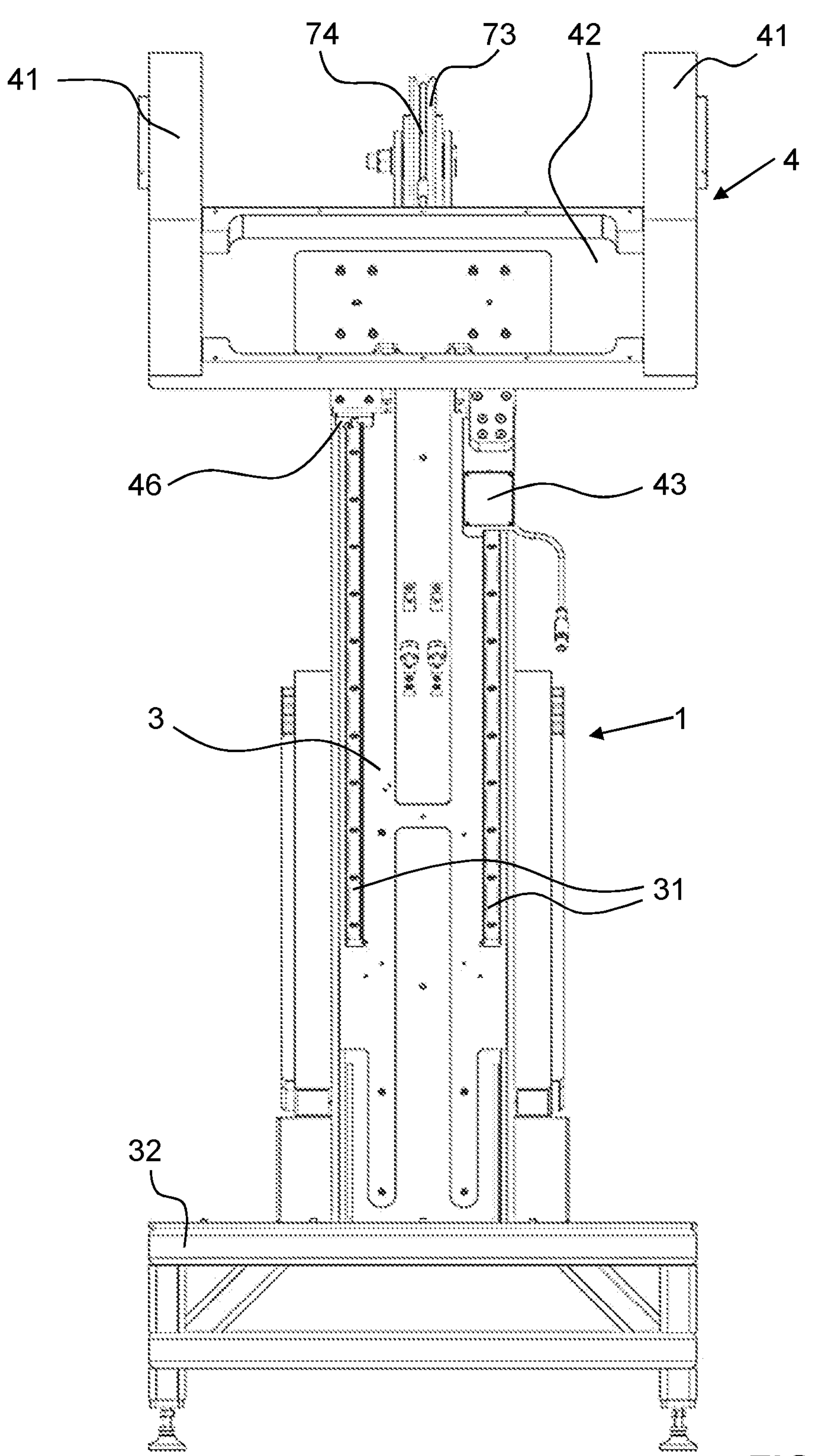
FIG. 8 shows a front view of the PET-scanning device of FIG. 7, without detector ring.
Figure 9:
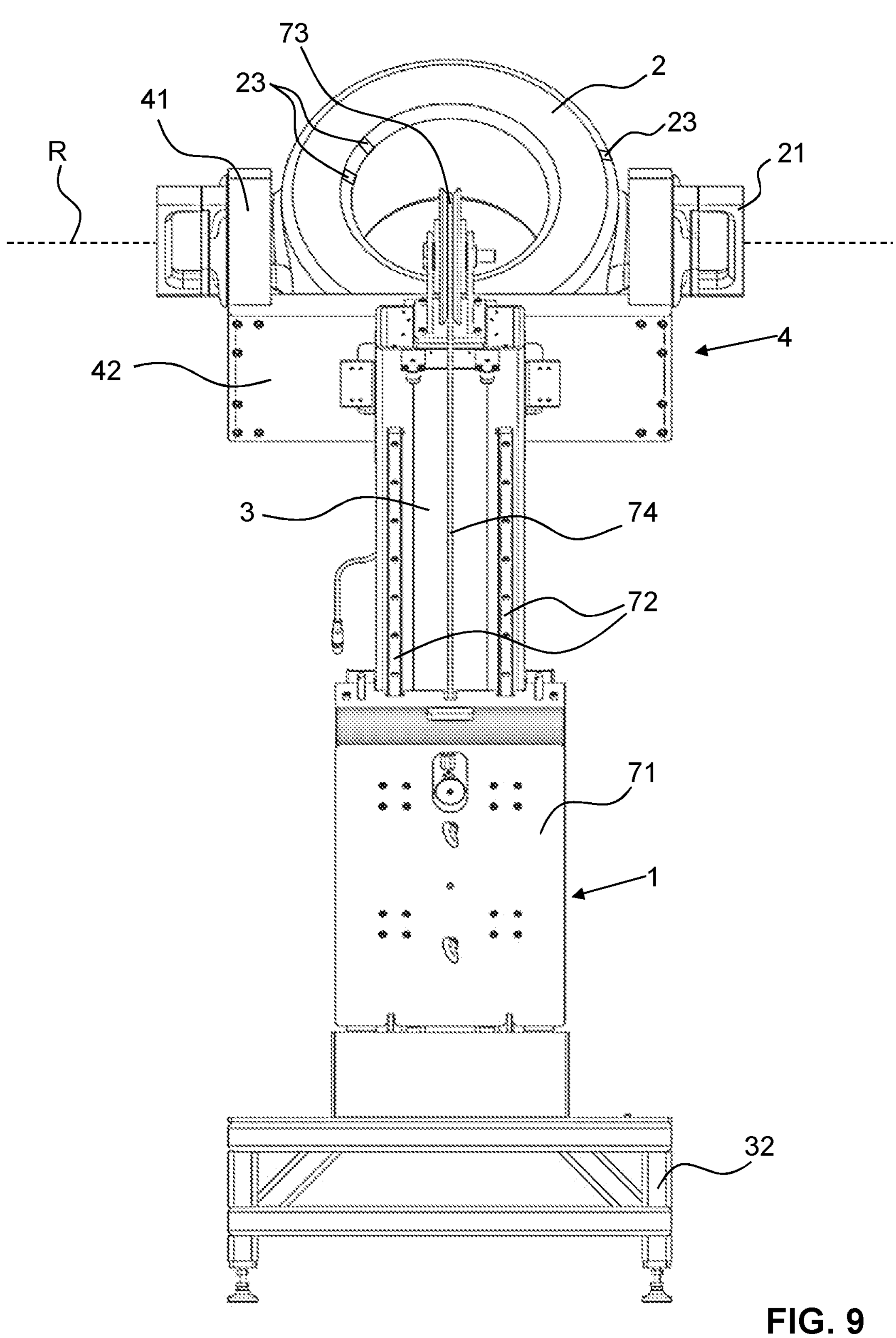
FIG. 9 shows a back view of the PET-scanning device of FIG. 7.
Figure 10:
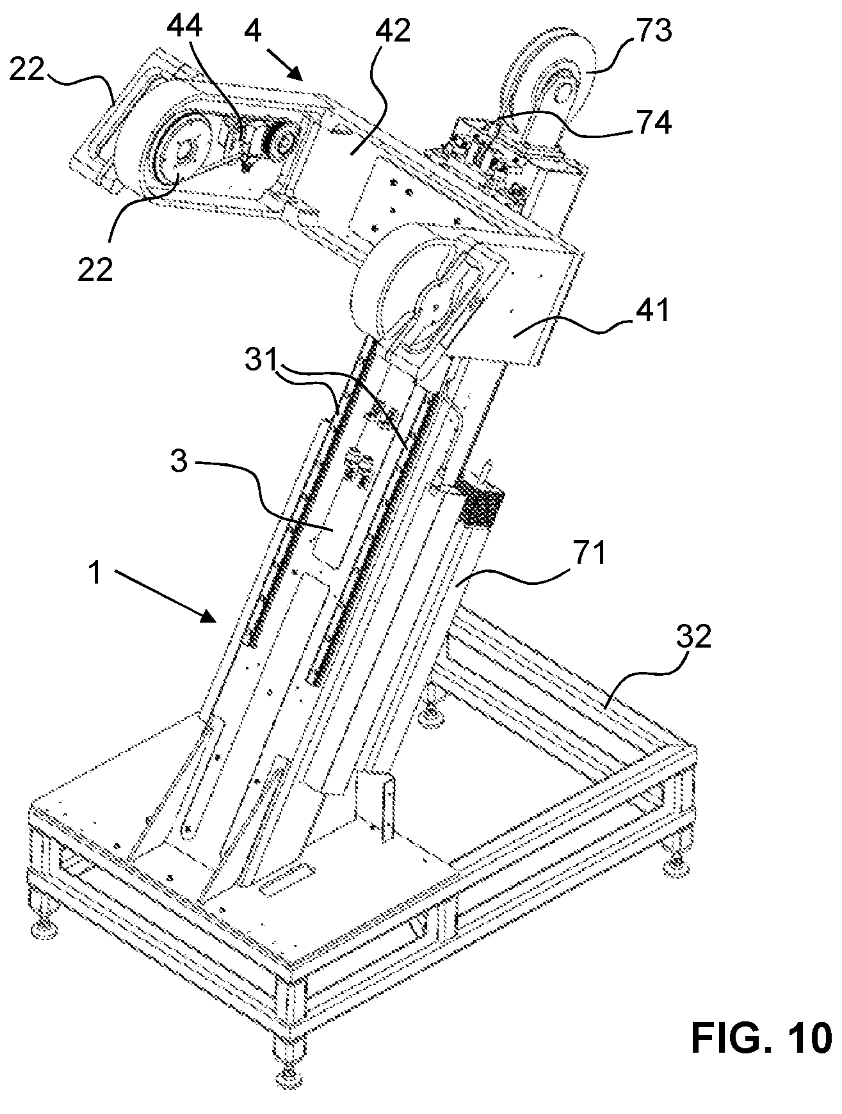
FIG. 10 shows a perspective view of the PET-scanning device of FIG. 7, without detector ring and with visible rotation drive unit.

FIGS. 7 to 11 show a further, particularly preferred embodiment of a PET-scanning device 1. In the view of FIGS. 7, 8 and 10, a guide rail 31 of the main supporting structure 3 is visible along which the U-shaped portion 4 is displaceable. The guide rail 31, which is present, but not necessarily visible, in all embodiments of FIGS. 1 to 14, here comprises two rail elements, which extend in parallel (see FIGS. 8 and 10). The guide rail 31 defines the direction of displacement of the U-shaped portion 4.

For facilitating the displacement of the U-shaped portion 4, a weight-compensation device 7 is provided. The weight-compensation device 7 comprises a counterweight 71, which is connected to the U-shaped portion 4 by means of a cable 74 and via a pulley 73. The pulley 73 is arranged on top of the main supporting structure 3 and guides the cable 74 from the U-shaped portion 4 to the counterweight 71. The counterweight 71 preferably has approximately the same weight as the entire displaceable unit form by the U-shaped portion 4 and the detector ring 2. In the present embodiment, the counterweight 71 is attached to the backside of the main supporting structure 3 by means of a guide rail 72 (see FIG. 9). Thus, the counterweight 71 is displaceable along the guide rail 72 which extends in parallel to the guide rail 31 along which the U-shaped portion 4 is displaceable. Similar as the guide rail 31, the guide rail 72 here also comprises two rail elements that extend in parallel.

The counterweight 71 as well as the pulley 73 and further parts of the PET-scanning device 1 are preferably covered by a cover due to design and safety reasons. For illustration purposes, however, the cover has been removed in the views of FIGS. 7 to 11 as well as in FIG. 12.

A weight-compensation device 7 as the one shown in FIGS. 7 to 10 is preferably present in all embodiments shown in FIGS. 1 to 11. Of course, it would also be conceivable that no weight-compensation device is provided or that a weight-compensation device is present, but is not based on a counterweight and a pulley. Instead, a weight-compensation device could be provided which is e.g. based on a gas pressure spring.

For preventing and unwanted displacement or rotation of the detector ring 2 in particular during the scanning procedure, a brake device for preventing an undesired displacement of the U-shaped portion 4 along the guide rail 31 and a brake device for preventing an undesired rotation of the detector ring about the axis of rotation are preferably provided in all embodiments. The brake devices are preferably electromagnetically actuated devices, in order that they can be operated automatically by the computing device 5. The computing device 5 can particularly be adapted to block any displacement and rotation of the detector ring 2 during image acquisition.

In the embodiment of FIGS. 7 to 11, a displacement brake device 43 for preventing an undesired displacement of the U-shaped portion 4 is fixedly attached to the U-shaped portion 4 in such a way that its brake elements can act directly on the guide rail 31 (see FIG. 8).

Figure 11:
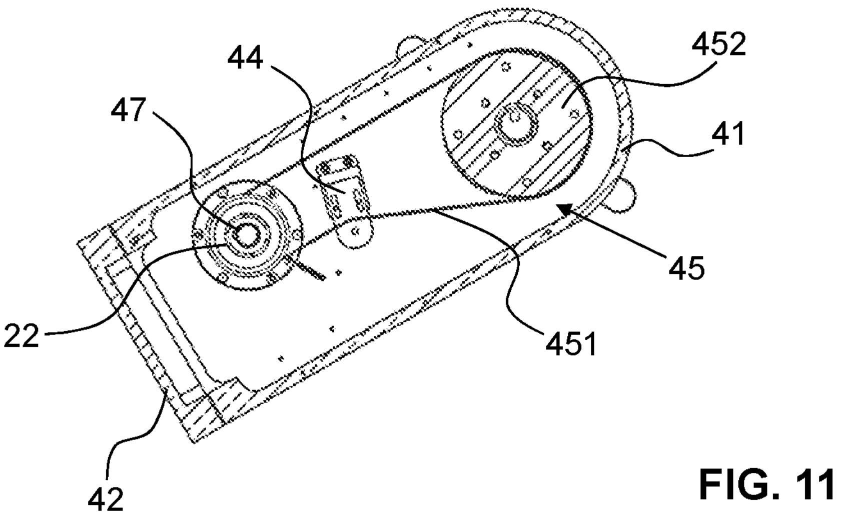
FIG. 11 shows a detailed view of the rotation drive unit and the rotation brake device of the PET-scanning device of FIG. 10.

A rotation brake device 44 for preventing an undesired rotation of the detector ring 2 is shown in FIG. 10 and particularly in the detail view of FIG. 11. The rotation brake device 44 is arranged in one or both of the holding arms 41 and comprises in each case a brake element that acts on a toothed belt 451 which connects the fixation lug 22 with a drive wheel 452 that is also arranged with the holding arm 41. By blocking the movement of the toothed belt 451, a rotation of the detector ring 2 can be prevented by the rotation brake device 44.

For facilitating displacement and rotation of the detector ring 2 for the user, a handle 21 is provided on the outer side of each fixation lug 22. The handles 21 can comprise a switch to actively enable displacement and rotation, i.e. to operate brake devices 43 and 44 such that displacement and/or rotation of the detector ring 2 becomes possible. Additionally or alternatively, one or more handles could for example also be provided directly on the detector ring 2.

Movements of the detector ring 2 relative to the main supporting structure 3 can be further facilitated for the user in all embodiments by means of a displacement drive unit and/or a rotation drive unit. FIG. 11 shows a rotation drive unit 45 comprising the drive wheel 452. The drive wheel 452 can be driven by a motor 453, which cannot be seen in FIG. 11, but in FIG. 12. The rotation of the toothed drive wheel 452 is transferred to the fixation lug 22 by means of the toothed belt 451. By rotating the fixation lug 22, the detector ring 2 is rotated about the axis of rotation R. Due to design and safety reasons, the inner sides of the holding arms 41 preferably comprise a cover for covering the rotation drive unit 45. For illustration purposes, however, these covers have been removed in FIGS. 10 to 12.

The displacement drive unit is not visible in FIGS. 8 to 12, but can be provided. For example, the pulley 73 can be driven or one or more additional cables can be attached to the U-shaped portion 4 and be wound on a spool that is coupled to a motor. By means of rotating the one or more spools, the U-shaped portion 4 can then be pulled upwards or downwards. A displacement drive unit 34 having a worm shaft 341 is described further below with respect to FIG. 12.

For detecting the position of the U-shaped portion 4 along the guide rail 31, a detector displacement encoder 46 is preferably provided in all embodiments. In the embodiment of FIGS. 8 to 12, the detector displacement encoder 46 is attached to the U-shaped portion 4, as can be seen in FIG. 8.

For detecting the angle of rotation of the detector ring 2 about the axis of rotation R, a detector rotation encoder 47 is preferably provided in all embodiments. In the embodiment of FIGS. 8 to 12, the detector rotation encoder 47 is provided on one of the fixation lugs 22, as can be seen in FIG. 11.

The detector displacement encoder 46 and the detector rotation encoder 47 are preferably connected either by means of cables or wirelessly to the computing device 5.

FIG. 9 also shows the provision of balancing weights 23 which are attached to the detector ring 2. The balancing weights 23 serve to balance the detector ring 2 such, that the axis of Rotation extends through the centre of mass of the detector ring 2. For this purpose, the balancing weights 23 can be movable e.g. along the circumference of the detector ring 2 and/or they can be detachably attachable to the detector ring 2, meaning that they can be removed from the detector ring 2 as required. The balancing weights 23 can be attachable to the inner surface and/or to the outer surface or to any other part of the detector ring 2. Of course, the provision of balancing weights on the detector ring is also possible in all other embodiments, even though this is not shown in the figures.

Figure 12:
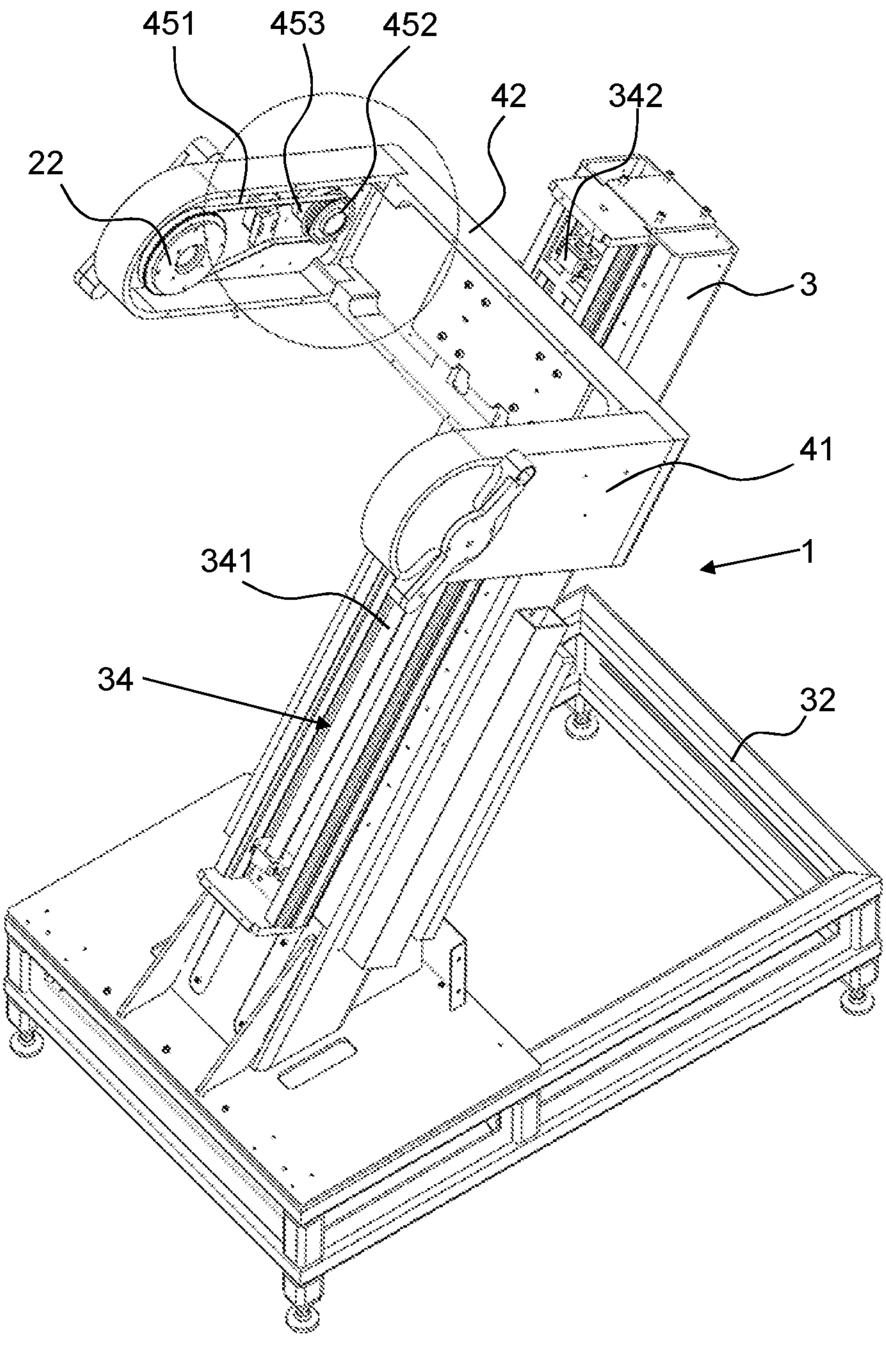
FIG. 12 shows a perspective view of an inventive PET-scanning device according to a fifth embodiment, without detector ring.

FIG. 12 shows another embodiment of a PET-scanning device 1 which does not comprise a weight-compensation device. By not having a counterweight with respect to the U-shaped portion 4 and the detector ring 2, the PET-scanning device 1 can be made more lightweight.

For displacing the U-shaped portion 4, the embodiment of FIG. 12 has a displacement drive unit 34 with a worm shaft 341. A motor 342 is provided as a drive for rotating the worm shaft 341 about its longitudinal center axis. The worm shaft 341 engages with a threaded element (not visible in FIG. 12) of the U-shaped portion 4 in such a way that a rotation of the worm shaft 341 results in a displacement of the U-shaped portion 4 along the guide rail 31. The worm shaft 341 also serves to prevent an undesired displacement of the U-shaped portion 4.

Figure 13:
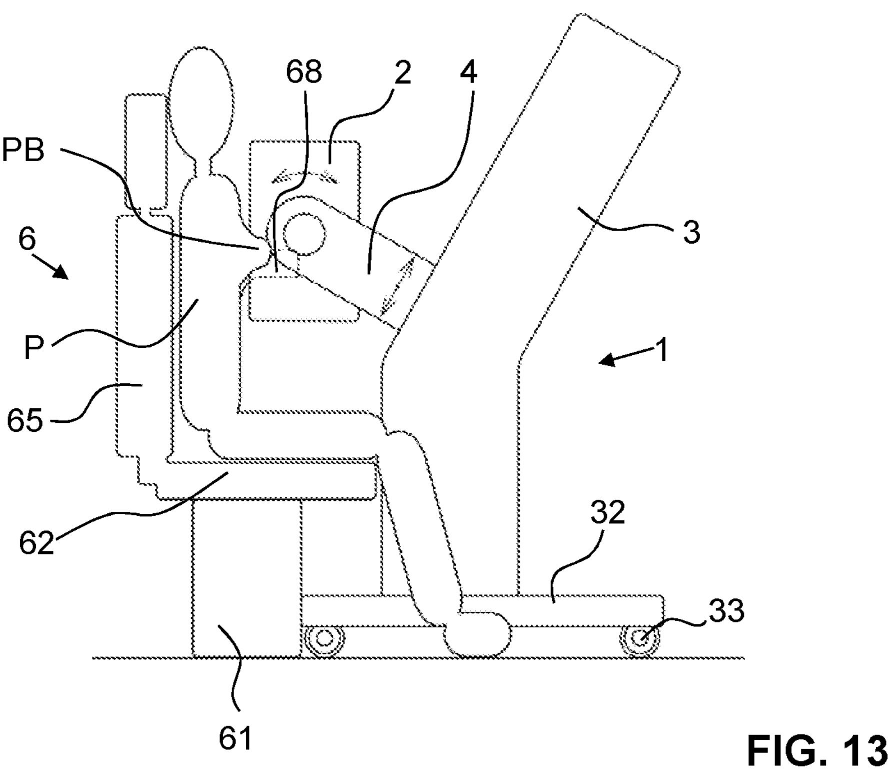
FIG. 13 shows a schematic side view of the same PET-scanning device as in FIG. 1, with a support device on that allows imaging of a patient's breast, with the patient being in a sitting position.

In FIG. 13, the same PET-scanning device 1 is shown as in FIG. 1. The PET-scanning device 1 is here used to image the breast of a female patient P. The PET-scan can particularly be used in the field of oncology, i.e. to detect and/or measure carcinogenic tissue within the patient's breast PB. For this purpose, the patient P is sitting, during the image acquisition, on a scanning support 6 in the form of a seating unit. The seating unit comprises a breast support 68, which can be attached e.g. to the backrest 65 and serves to support the patient's breast PB during the PET-scanning procedure. For the PET-scanning, the breast support 68, with the patient's breast on top of it, is inserted into the opening of the detector ring 2. The detector ring 2 is preferably rotated into a vertical orientation and displaced to a lower position of the main supporting structure 3 for this purpose, as shown in FIG. 13. The breast support 68 does not necessarily have to be attached to another part of the scanning support 6, but could alternatively also form a separate part of the scanning support 6. For example, the breast support 68 could also be in the form of an insert that can be attached to the inside of the detector ring 2. In another embodiment, the breast support 68 could also be attachable to the upper body of the patient P. In any case, the breast support 68 can have an indentation, in order to ergonomically accommodate the patient's breast PB.

Figure 14:
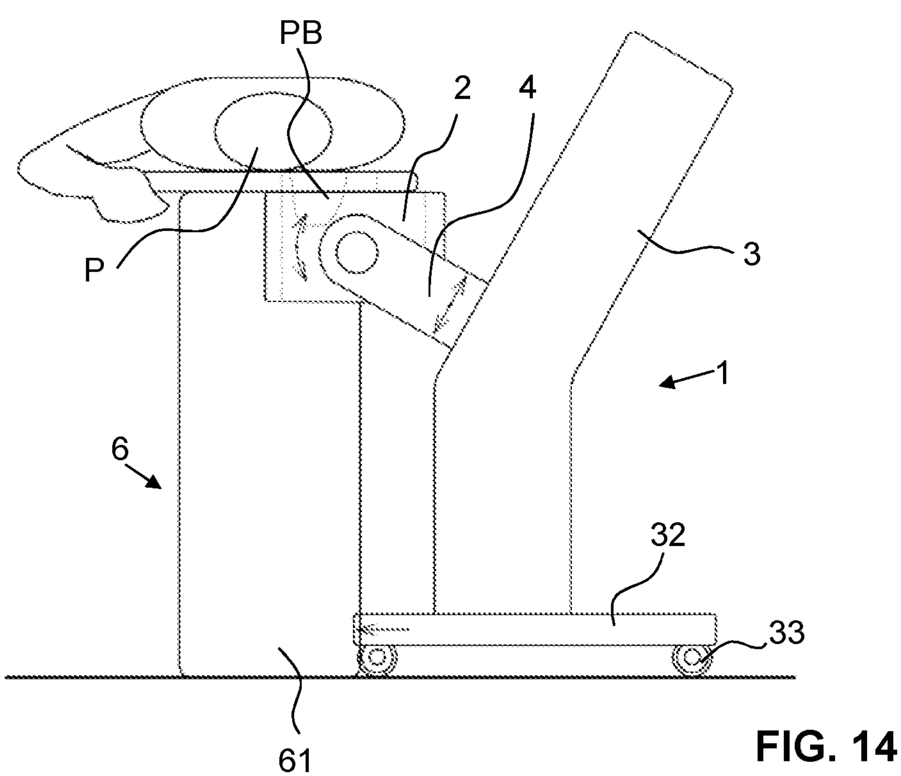
FIG. 14 shows a schematic side view of the same PET-scanning device as in FIG. 1, with a support device on that allows imaging of a patient's breast, with the patient being in a lying position.

FIG. 14 shows another embodiment, in which the scanning support 6 is also adapted to scan a breast of a patient P. However, the patient P is here in a prone position during the image acquisition. The scanning support 6 comprises an opening or an indentation which allows the patient's breast PB to hang/extend into the detector ring 2, which is oriented horizontally for the PET-scan, as shown in FIG. 14.

The present invention is of course not limited on the embodiments as described and as shown in FIGS. 1 to 14. The elements presented with respect to the different embodiments of FIGS. 1 to 14 can of course be exchanged and combined between the embodiments and many modifications are possible. Features that have been indicated with respect to certain embodiments only, can well be provided on other embodiments, too. For example, the counterweight 71 does not necessarily be arranged on the opposite side of the main supporting structure 3 with respect to the U-shaped portion 4, but could also be arranged on the same side or inside of the main supporting structure 3. Wheels for making it easier to move of the PET-scanning device can be provided in all embodiments, but they could also be omitted. The guide rail for guiding the U-shaped portion 4 could also comprise a single rail element only or more than two rail elements. Instead of being driven, the U-shaped portion 4 could also be displaceable and/or rotatable by hand, i.e. by means of muscle force. A scanning support 6 does not necessarily be provided. A plurality of further modifications is possible.

The invention claimed is:

1. A positron emission tomography (PET)-scanning device comprising:

a detector ring for detecting emitted PET-radiation; and a main supporting structure to which is attached a U-shaped portion with two arms for holding the detector ring between the arms;

wherein the detector ring is held by the two arms in such a way that the detector ring can be rotated about an axis of rotation that extends through the U-shaped portion, in particular through the two arms of the U-shaped portion, wherein the main supporting structure comprises a guide rail to which the U-shaped portion is attached in such a way, that the U-shaped portion can be displaced along the guide rail, and wherein the guide rail extends along an inclined direction relative to the direction of gravity.

2. The PET-scanning device according to claim 1, wherein the main supporting structure and the U-shaped portion together form a Z-shaped structure.

3. The PET-scanning device according to claim 1, additionally comprising a weight-compensation device for compensating the weight of the U-shaped portion and the detector ring, in order to facilitate the displacement of the U-shaped portion along the guide rail for the user.

4. The PET-scanning device according to claim 3, wherein the weight-compensation-device comprises a counterweight, which is connected to the U-shaped portion via a pulley, and which is preferably arranged on the opposite side of the main supporting structure with respect to the U-shaped portion.

5. The PET-scanning device according to claim 4, wherein the counterweight is attached to a further guide rail in such a way, that the counterweight can be displaced along the further guide rail.

6. The PET-scanning device according to claim 1, wherein a first motor unit is provided for displacing the U-shaped portion along the guide rail.

7. The PET-scanning device according to claim 1, wherein a second motor unit is provided for rotating the detector ring about the axis of rotation.

8. The PET-scanning device according to claim 1, additionally comprising a first brake device for preventing an undesired displacement of the U-shaped shaped portion along the guide rail.

9. The PET-scanning device according to claim 8, wherein the first brake device is an electromagnetically actuated brake device, which generates a braking effect when not activated and releases the braking effect upon activation.

10. The PET-scanning device according to claim 1, additionally comprising a second brake device for preventing an undesired rotation of the detector ring about the axis of rotation.

11. The PET-scanning device according to claim 10, wherein the second brake device is an electromagnetically actuated brake device, which generates a braking effect when not activated and releases the braking effect upon activation.

12. The PET-scanning device according to claim 1, wherein the axis of rotation, about which the detector ring can be rotated, extends through the centre of mass of the detector ring.

13. The PET-scanning device according to claim 1, additionally comprising one or more weights, which are movably attached to the detector ring and/or which are detachably attachable to the detector ring, in order to balance the centre of mass of the detector ring with respect to the axis of rotation.

14. The PET-scanning device according to claim 1, wherein the two arms of the U-shaped portion extend obliquely upwards in relation to the direction of gravity.

15. The PET-scanning device according to claim 1, wherein the PET-scanning device comprises one or more detector encoders, in particular one or more electronic detector encoders, for detecting the displacement position of the U-shaped portion along the guide rail and/or the rotation angle of the detector ring about the axis of rotation.

16. The PET-scanning device according to claim 1, additionally comprising a scanning support, which allows a subject to be scanned, preferably a human patient, to be positioned, preferably in a sitting or lying position, with respect to the detector ring for a PET-scanning procedure, wherein the scanning support comprises one or more support encoders, in particular one or more electronic support encoders, for detecting the position of the patient.

17. The PET-scanning device according to claim 16, wherein the scanning support is adapted to position a patient's breast within the detector ring.

18. A positron emission tomography (PET)-scanning device comprising:

a detector ring for detecting emitted PET-radiation; and a main supporting structure to which is attached a U-shaped portion with two arms for holding the detector ring between the arms;

wherein the detector ring is held by the two arms and configured so that the detector ring is rotatable about an axis of rotation that extends through the U-shaped portion through the two arms of the U-shaped portion, wherein the main supporting structure comprises a guide rail to which the U-shaped portion is attached so that the U-shaped portion is displaceable along the guide rail, and wherein the guide rail extends along an inclined direction relative to the direction of gravity, wherein the inclined direction is at an angle that is neither parallel nor perpendicular to the direction of gravity.

19. The PET-scanning device according to claim 17, wherein the inclined direction is at an angle between 10° and 50°.

20. The PET-scanning device according to claim 17, wherein the inclined direction is at an angle between 20° and 40°.

* * * * *